US008916045B2

(12) United States Patent
Reinbigler et al.

(10) Patent No.: US 8,916,045 B2
(45) Date of Patent: Dec. 23, 2014

(54) INSTALLATION FOR TREATING A BIOLOGICAL LIQUID

(75) Inventors: Rene Reinbigler, Kirchheim (FR);
Jean-Louis Weissenbach, Ville (FR);
Cecile Delbos, Eschau (FR)

(73) Assignee: EMD Millipore Corporation, Billerica, MA (US)

( * ) Notice: Subject to any disclaimer, the term of this patent is extended or adjusted under 35 U.S.C. 154(b) by 148 days.

(21) Appl. No.: 13/430,734

(22) Filed: Mar. 27, 2012

(65) Prior Publication Data

US 2012/0248025 A1    Oct. 4, 2012

(30) Foreign Application Priority Data

Mar. 28, 2011  (FR) ..................................... 11 52556

(51) Int. Cl.
| | | |
|---|---|---|
| *B01D 35/00* | (2006.01) | |
| *B01D 29/52* | (2006.01) | |
| *C12M 1/00* | (2006.01) | |
| *C12M 3/00* | (2006.01) | |
| *B01D 29/00* | (2006.01) | |

(52) U.S. Cl.
CPC ............... *C12M 47/12* (2013.01); *C12M 23/44* (2013.01)
USPC .............. 210/253; 210/85; 210/206; 210/241; 210/249; 210/250; 210/258; 210/257.1; 210/260; 422/534

(58) Field of Classification Search
None
See application file for complete search history.

(56) References Cited

U.S. PATENT DOCUMENTS

| | | |
|---|---|---|
| 2,413,853 A | 1/1947 | Zademach et al. |
| 2,787,403 A | 4/1957 | Carr et al. |

(Continued)

FOREIGN PATENT DOCUMENTS

| | | |
|---|---|---|
| CN | 101281204 A | 10/2008 |
| DE | 10 2006 059 459 A1 | 7/2008 |

(Continued)

OTHER PUBLICATIONS

French Search Report dated Feb. 9, 2009 in co-pending foreign patent application No. FR 0853629.

(Continued)

*Primary Examiner* — Benjamin Kurtz
(74) *Attorney, Agent, or Firm* — Nields, Lemack & Frame, LLC (57) ABSTRACT

The invention concerns an installation for treating biological liquid comprising a platform provided with an edge running front-to-back, a pump (105), a filtration assembly (111, 150), a pre-filtration assembly (114) having an inlet point and an outlet point respectively belonging to first and second T-shaped branching connectors (137, 156), two pre-filtration components (115a, 115b) aligned in a front-to-back direction on said platform along said front-to-back edge and each provided with inlet (157, 158) and outlet (159, 151) nozzles, said installation comprising first and second conduits (152, 153) connected to said first T-shaped connector and respectively to said inlet nozzles and third and fourth conduits (154, 155) connected to said second T-shaped connector and respectively to said outlet nozzles (159, 151), which inlet and outlet nozzles and conduits are on an opposite side of said pre-filtration components (105) to said front-to-back edge of said platform.

15 Claims, 4 Drawing Sheets

(56) References Cited

U.S. PATENT DOCUMENTS

| | | | |
|---|---|---|---|
| 3,022,229 A | 2/1962 | Heden | |
| 3,179,117 A | 4/1965 | Gibson et al. | |
| 3,667,487 A | 6/1972 | Schoenbeck et al. | |
| 3,772,154 A | 11/1973 | Isenberg et al. | |
| 3,774,762 A | 11/1973 | Lichtenstein | |
| 4,113,623 A | 9/1978 | Koether et al. | |
| 4,332,750 A | 6/1982 | Roggenburg, Jr. et al. | |
| 4,370,983 A | 2/1983 | Lichtenstein | |
| 4,784,751 A | 11/1988 | McGehee | |
| 4,790,118 A | 12/1988 | Chilcoate | |
| 4,852,851 A | 8/1989 | Webster | |
| 4,855,236 A | 8/1989 | Levin | |
| 4,915,119 A | 4/1990 | Franklin | |
| 5,019,257 A * | 5/1991 | Suzuki et al. | 210/253 |
| 5,141,866 A | 8/1992 | Levin | |
| 5,265,912 A | 11/1993 | Natividad | |
| 5,290,518 A | 3/1994 | Johnson | |
| 5,342,463 A | 8/1994 | Addeo et al. | |
| 5,520,885 A | 5/1996 | Coelho et al. | |
| 5,628,908 A | 5/1997 | Kamen et al. | |
| 5,645,723 A | 7/1997 | Fujishiro et al. | |
| 5,678,568 A | 10/1997 | Uchikubo et al. | |
| 5,711,916 A | 1/1998 | Riggs et al. | |
| 5,738,645 A | 4/1998 | Plotkin | |
| 5,985,653 A | 11/1999 | Armstrong et al. | |
| 6,073,942 A | 6/2000 | Heneveld, Sr. | |
| 6,129,099 A | 10/2000 | Foster et al. | |
| 6,146,124 A | 11/2000 | Coelho et al. | |
| 6,186,998 B1 | 2/2001 | Inuzuka et al. | |
| 6,213,334 B1 | 4/2001 | Coelho et al. | |
| 6,228,255 B1 | 5/2001 | Peterson et al. | |
| 6,232,115 B1 | 5/2001 | Coelho et al. | |
| 6,303,025 B1 | 10/2001 | Houchens | |
| 6,361,642 B1 | 3/2002 | Bellamy et al. | |
| 6,670,169 B1 | 12/2003 | Schob et al. | |
| 6,808,675 B1 | 10/2004 | Coelho et al. | |
| 6,902,706 B1 | 6/2005 | Colin et al. | |
| 6,982,063 B2 | 1/2006 | Hamel et al. | |
| 7,153,286 B2 | 12/2006 | Busby et al. | |
| 7,326,355 B2 | 2/2008 | Graetz et al. | |
| 7,485,224 B2 | 2/2009 | Jones et al. | |
| 7,648,627 B2 | 1/2010 | Beden et al. | |
| 7,666,602 B2 | 2/2010 | Ammann et al. | |
| 7,867,189 B2 | 1/2011 | Childers et al. | |
| 7,935,074 B2 | 5/2011 | Plahey et al. | |
| 7,935,253 B2 | 5/2011 | Beulay et al. | |
| 8,114,276 B2 | 2/2012 | Childers et al. | |
| 8,163,172 B2 | 4/2012 | Beulay et al. | |
| 8,343,356 B2 | 1/2013 | Beulay et al. | |
| 8,383,397 B2 | 2/2013 | Wojciechowski et al. | |
| 8,505,959 B2 | 8/2013 | Darling, III | |
| 8,506,798 B2 | 8/2013 | Beulay et al. | |
| 8,557,113 B2 | 10/2013 | Beulay et al. | |
| 2003/0040104 A1 | 2/2003 | Barbera-Guillem | |
| 2004/0031507 A1 | 2/2004 | Ross et al. | |
| 2004/0104153 A1 | 6/2004 | Yang | |
| 2004/0222341 A1 | 11/2004 | Breda et al. | |
| 2004/0259240 A1 | 12/2004 | Fadden | |
| 2005/0254879 A1 | 11/2005 | Gundersen et al. | |
| 2006/0024212 A1 | 2/2006 | Hwang | |
| 2006/0057030 A1 | 3/2006 | Lee et al. | |
| 2006/0118472 A1 | 6/2006 | Schick et al. | |
| 2006/0226333 A1 | 10/2006 | Newkirk | |
| 2007/0095364 A1 | 5/2007 | Watt | |
| 2007/0112297 A1 | 5/2007 | Plahey et al. | |
| 2007/0128087 A1 | 6/2007 | Cannizzaro et al. | |
| 2007/0199875 A1 | 8/2007 | Moorey et al. | |
| 2008/0023045 A1 | 1/2008 | Miller et al. | |
| 2008/0057274 A1 | 3/2008 | Hagiwara et al. | |
| 2008/0213143 A1 | 9/2008 | Gyonouchi et al. | |
| 2008/0254962 A1 | 10/2008 | Mizuo et al. | |
| 2009/0050756 A1 | 2/2009 | Newkirk et al. | |
| 2009/0101219 A1 | 4/2009 | Martini et al. | |
| 2009/0101552 A1 | 4/2009 | Fulkerson et al. | |
| 2009/0111179 A1 | 4/2009 | Hata et al. | |
| 2009/0180933 A1 | 7/2009 | Kauling et al. | |
| 2009/0215602 A1 | 8/2009 | Min et al. | |
| 2009/0294349 A1 * | 12/2009 | Beulay et al. | 210/416.1 |
| 2009/0314970 A1 | 12/2009 | McAvoy et al. | |
| 2010/0108920 A1 | 5/2010 | Tatarek | |
| 2010/0126927 A1 | 5/2010 | Blankenstein et al. | |
| 2010/0187167 A1 | 7/2010 | Reinbigler et al. | |
| 2010/0204765 A1 | 8/2010 | Hall et al. | |
| 2010/0206785 A1 * | 8/2010 | Beulay et al. | 210/85 |
| 2010/0234805 A1 | 9/2010 | Kaufmann et al. | |
| 2011/0174716 A1 | 7/2011 | Beulay et al. | |
| 2011/0297866 A1 | 12/2011 | Weber | |
| 2011/0303306 A1 | 12/2011 | Weber | |
| 2012/0006736 A1 | 1/2012 | Cirou et al. | |
| 2012/0018018 A1 | 1/2012 | Cirou et al. | |
| 2012/0031510 A1 | 2/2012 | Weissenbach et al. | |
| 2012/0138173 A1 | 6/2012 | Cirou et al. | |
| 2012/0138522 A1 | 6/2012 | Cirou et al. | |
| 2012/0145616 A1 | 6/2012 | Weissenbach et al. | |
| 2012/0160342 A1 | 6/2012 | Weissenbach et al. | |
| 2012/0160356 A1 | 6/2012 | Reinbigler et al. | |
| 2012/0168390 A1 | 7/2012 | Beulay et al. | |
| 2013/0087490 A1 | 4/2013 | Beulay et al. | |
| 2013/0193073 A1 | 8/2013 | Hogard et al. | |
| 2013/0210130 A1 | 8/2013 | Larcher et al. | |
| 2013/0236130 A1 | 9/2013 | Cirou et al. | |
| 2013/0240065 A1 | 9/2013 | Weissenbach et al. | |
| 2014/0069537 A1 | 3/2014 | Cirou et al. | |

FOREIGN PATENT DOCUMENTS

| | | |
|---|---|---|
| DE | 10 2008 003 823 A1 | 7/2008 |
| EP | 0479047 A2 | 4/1992 |
| EP | 0803723 A1 | 10/1997 |
| EP | 1195171 A2 | 4/2002 |
| EP | 1239277 A1 | 9/2002 |
| EP | 2044964 A2 | 4/2009 |
| EP | 2130903 A1 | 12/2009 |
| EP | 2208534 A1 | 7/2010 |
| EP | 2228635 A1 | 9/2010 |
| FR | 2241615 A1 | 3/1975 |
| FR | 2673853 A1 | 9/1992 |
| FR | 2931838 A1 | 12/2009 |
| FR | 2940145 A1 | 6/2010 |
| GB | 1434786 A | 5/1976 |
| GB | 2448858 A | 11/2008 |
| JP | 62-081543 A | 4/1987 |
| JP | 2010-502405 A | 1/2010 |
| WO | 00/48703 A1 | 8/2000 |
| WO | 2005/090403 A2 | 9/2005 |
| WO | 2006/043895 A1 | 4/2006 |
| WO | 2007/094254 A1 | 8/2007 |
| WO | 2008/033788 A2 | 3/2008 |
| WO | 2008/064242 A2 | 5/2008 |
| WO | 2008/071351 A1 | 6/2008 |
| WO | 2008/120021 A1 | 10/2008 |
| WO | 2009/017614 A1 | 2/2009 |
| WO | 2009/073567 A1 | 6/2009 |
| WO | 2009/157852 A1 | 12/2009 |
| WO | 2010/084432 A1 | 7/2010 |
| WO | 2010/094249 A1 | 8/2010 |

OTHER PUBLICATIONS

French Search Report dated Sep. 24, 2010 in co-pending foreign patent application No. FR 1050209.

French Search Report dated Nov. 25, 2010 in co-pending foreign patent application No. FR 1054514.

French Search Report dated Nov. 12, 2010 in co-pending foreign patent application No. FR 1055025.

French Search Report dated Feb. 3, 2011 in co-pending foreign patent application No. FR 1055026.

French Search Report dated May 24, 2011 in co-pending foreign patent application No. FR 1056421.

Extended European Search Report for co-pending foreign patent application No. EP 09290938.1.

French Search Report dated Nov. 22, 2010 in co-pending foreign patent application No. FR 1054517.

(56) References Cited

OTHER PUBLICATIONS

French Search Report dated Nov. 22, 2010 in co-pending foreign patent application No. FR 1054516.
French Search Report dated Nov. 17, 2011 in corresponding foreign patent application No. FR 1152556.
Office Action mailed Jun. 11, 2012 in co-pending U.S. Appl. No. 13/420,906.
Office Action mailed Jun. 5, 2012 in co-pending U.S. Appl. No. 12/592,901.
Notice of Allowance mailed Jun. 18, 2013 in U.S. Appl. No. 13/688,255, now US Patent No. 8,506,798.
French Search Report dated Oct. 16, 2009 in co-pending French Patent Application No. FR 0950435.
International Search Report/Written Opinion mailed Sep. 30, 2011 in co-pending PCT Application No. PCT/IB2011/052447.
International Search Report/Written Opinion mailed Sep. 28, 2011 in co-pending PCT Application No. PCT/IB2011/052450.
International Search Report mailed Jun. 8, 2011 in co-pending PCT Application No. PCT/IB2011/050089.
International Search Report mailed Sep. 29, 2011 in co-pending PCT Application No. PCT/IB2011/052676.
International Search Report mailed Aug. 29, 2011 in co-pending PCT Application No. PCT/IB2011/052679.
International Search Report mailed Aug. 2, 2011 in co-pending PCT Application No. PCT/IB2011/052448.
Office Action-Restriction-mailed Jan. 27, 2012 in co-pending U.S. Appl. No. 12/685,140.
Office Action mailed Jun. 28, 2012 in co-pending U.S. Appl. No. 12/685,140.
Office Action—Restriction—mailed Oct. 15, 2013 in co-pending U.S. Appl. No. 13/004,425.
Office Action mailed Oct. 9, 2013 in co-pending U.S. Appl. No. 13/116,508.
Office Action mailed Oct. 18, 2013 in co-pending U.S. Appl. No. 13/116,508.
Notice of Allowance mailed Sep. 6, 2013 in co-pending U.S. Appl. No. 12/592,901, now US Patent No. 8,557,113.
Office Action mailed Oct. 23, 2013 in co-pending U.S. Appl. No. 13/153,809.
Notice of Allowance mailed Oct. 17, 2012 in U.S. Appl. No. 13/420,906, now US Patent No. 8,343,356.
Written Opinion of the International Searching Authority mailed Jun. 8, 2011 in co-pending PCT application No. PCT/IB2011/050089.
International Preliminary Report on Patentability mailed Jul. 26, 2012 in co-pending PCT application No. PCT/IB2011/050089.
International Preliminary Report on Patentability mailed Dec. 20, 2012 in co-pending PCT application No. PCT/IB2010/052447.
Written Opinion of the International Searching Authority mailed Sep. 29, 2011 in co-pending PCT application No. PCT/IB2011/052676.
International Preliminary Report on Patentability mailed Jan. 10, 2013 in co-pending PCT application No. PCT/IB2011/052676.
Written Opinion of the International Searching Authority mailed Aug. 29, 2011 in co-pending PCT application No. PCT/IB2011/052679.
International Preliminary Report on Patentability mailed Jan. 10, 2013 in co-pending PCT application No. PCT/IB2011/052679.
Written Opinion of the International Searching Authority mailed Aug. 2, 2011 in co-pending PCT application No. PCT/IB2011/052448.
International Preliminary Report on Patentability mailed Dec. 20, 2012 in co-pending PCT application No. PCT/IB2011/052448.
International Preliminary Report on Patentability mailed Dec. 20, 2012 in co-pending PCT application No. PCT/IB2011/052450.
International Search Report mailed Sep. 4, 2012 in corresponding PCT application No. PCT/IB2012/051424.
Office Action—Restriction—mailed Apr. 25, 2013 in co-pending U.S. Appl. No. 13/161,975.
Notice of Allowance mailed May 13, 2013 in co-pending U.S. Appl. No. 13/161,975.
Office Action mailed May 9, 2013 in co-pending U.S. Appl. No. 12/592,901.
Notice of Allowance mailed May 6, 2013 in co-pending U.S. Appl. No. 13/153,804.
Office Action mailed Feb. 22, 2013 in co-pending U.S. Appl. No. 13/688,255.
Notice of Allowance mailed Apr. 1, 2013 in co-pending U.S. Appl. No. 13/161,983.
Office Action—Restriction—mailed Apr. 2, 2013 in co-pending U.S Appl. No. 13/153,804.
Extended European Search Report and Search Opinion received for EP Patent Application No. 10290005.7, mailed on May 17, 2010, 5 pages.
International Preliminary Report on Patentability received for PCT application No. PCT/IB2010/050102, mailed on Aug. 4, 2011, 8 pages.
International Search Report and Written Opinion received for PCT application No. PCT/IB2010/050102, mailed on May 7, 2010, 10 pages.
Chinese Communication, with English translation, dated Sep. 27, 2012 in co-pending Chinese patent application No. CN 201010004496.1.
Final Rejection mailed Jan. 24, 2013 in co-pending U.S. Appl. No. 12/685,140.
Office Action mailed Oct. 25, 2013 in co-pending U.S. Appl. No. 13/187,698.
Office Action mailed Dec. 17, 2013 in co-pending U.S. Appl. No. 12/685,140.
Office Action mailed Jan. 16, 2014 in co-pending U.S. Appl. No. 13/004,425.
Notice of Allowance mailed Feb. 18, 2014 in co-pending U.S. Appl. No. 13/116,508.
Notice of Allowance mailed Mar. 18, 2014 in co-pending U.S. Appl. No. 13/116,508.
Final Rejection mailed Mar. 26, 2014 in co-pending U.S. Appl. No. 13/187,698.
Notice of Allowance mailed Apr. 1, 2014 in co-pending U.S. Appl. No. 13/153,809.
Notice of Allowance mailed Apr. 14, 2014 in co-pending U.S. Appl. No. 13/116,508.
Notice of Allowance mailed Apr. 14, 2014 in co-pending U.S. Appl. No. 13/153,809.
Final Rejection mailed Jun. 23, 2014 in co-pending U.S. Appl. No. 12/685,140.
Office Action mailed Jul. 24, 2014 in co-pending U.S. Appl. No. 13/187,698.
Office Action mailed Jul. 30, 2014 in co-pending U.S. Appl. No. 14/080,826.
Notice of Allowance mailed Sep. 3, 2014 in co-pending U.S. Appl. No. 13/116,508.
Notice of Allowance mailed Sep. 2, 2014 in co-pending U.S. Appl. No. 13/153,809.
Office Action mailed Aug. 25, 2014 in co-pending U.S. Appl. No. 13/004,425.
Notice of Allowance mailed Aug. 11, 2014 in co-pending U.S. Appl. No. 13/116,508.
Notice of Allowance mailed Aug. 08, 2014 in co-pending U.S. Appl. No. 13/153,809.
Korean communication, with English translation, dated Jul. 31, 2014 in co-pending Korean patent application No. 10-2013-7000355.
Korean communication, with English translation, dated Jul. 31, 2014 in co-pending Korean patent application No. KR 10-2013-7001692.
Korean communication, with English translation, dated Jul. 31, 2014 in co-pending Korean patent application No. KR 10-2013-7000366.
Korean communication, with English translation, dated Jul. 31, 2014 in co-pending Korean patent application No. KR 10-2013-7000356.
Notice of Allowance mailed Nov. 6, 2014 in co-pending U.S. Appl. No. 13/187,698.

* cited by examiner

INSTALLATION FOR TREATING A BIOLOGICAL LIQUID

The invention relates to installations for treating biological liquid, in particular, but not exclusively, for purifying a biopharmaceutical liquid in order to obtain a product such as monoclonal antibodies, vaccines or recombinant proteins.

It is known that biopharmaceutical liquids are in general obtained by cultures in a bioreactor and that they must then be purified to achieve the required characteristics of purity, concentration, absence of viruses, etc.

The purification is generally carried out by means of a succession of treatments such as clarification to eliminate the residues from the bioreactor culture and viral retention treatment sometimes followed by diafiltration treatment and concentration by tangential flow filtration (TFF). Other operations exist concerning purification, such as chromatography.

The purification treatments are essentially carried out by filtering operations in a circuit leading to a container for collecting the treated liquid. A number of types of container containing liquids can be connected to the inlet of the circuit, such as the source container that contains the product to be treated, but also the containers containing a cleaning liquid such as sodium hydroxide (NaOH), a rinsing liquid such as pure water or a buffer liquid such as a saline solution.

In addition to the container for collecting the treated liquid, various other containers for collecting cleaning, rinsing or buffer liquid, or for collecting residues, can be connected to the outlet of the circuit.

In a production context the liquid treatments can be carried out sequentially, the collection container for the first treatment potentially becoming the source container for the next treatment, and so on until the last treatment is carried out.

These treatments are conventionally carried out in dedicated installations comprising stainless steel pipes and other parts such as tanks or housings for filters, which necessitate operations before and after the actual treatment, which are relatively onerous, in particular operations of cleaning after use.

Within the last few years, these treatments have alternatively been carried out in installations in which the components in contact with the liquid are single-use components. Such an installation is known from the document EP 2 130 903.

Figure 1:
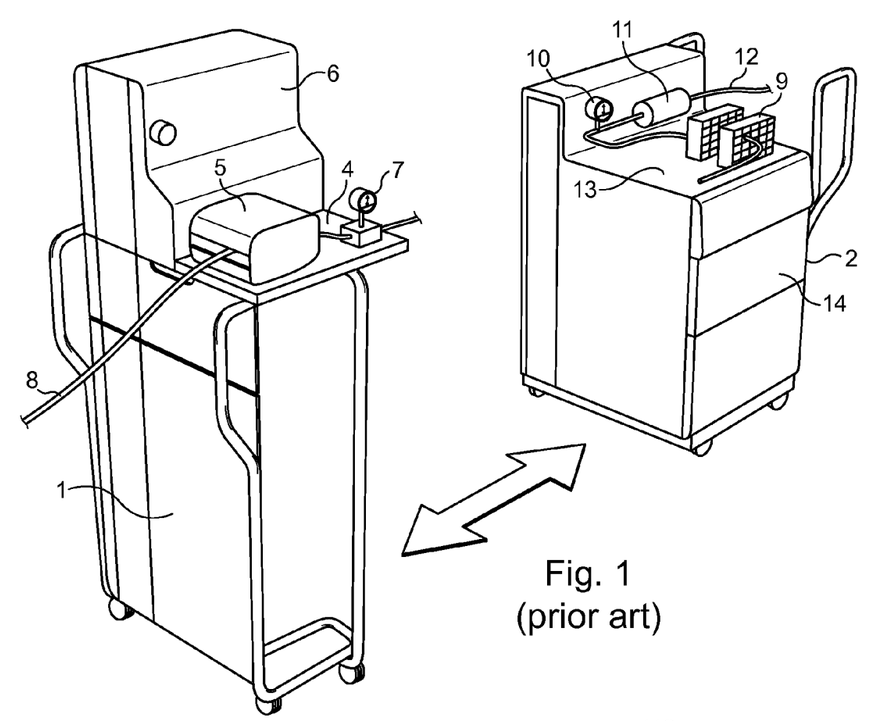

This installation, which is illustrated in FIG. 1, comprises a first cart 1 and a second cart 2 here in a separated configuration, i.e. with the second cart 2 moved away from the first cart 1. The second cart 2 is adapted to be nested in the first cart 1. Each cart 1 and 2 is of parallelepiped general shape and is mounted on wheels in order to enable its easy movement within a production zone.

The first cart 1 is open on one side and towards the ground, and its interior is hollowed to enable the nesting of the second cart 2. On the upper part of the first cart 1 is a support platform 4 adapted to receive re-usable components of the circuit and means for supporting the disposable components. Among the re-usable components carried by the platform 4 is in particular a flow pump 5, a first pressure sensor 7, and a control panel 6 for controlling the pump 5. The platform 4 is positioned at a sufficient height for the second cart 2 to be slid under it and be positioned, at least partially, under the circulation pump in its nested configuration.

The second cart 2 has a platform provided with an upper face 13 on which are positioned disposable components such as filter components 9 and 11 and re-usable components such as a second pressure sensor 10. This second cart 2 furthermore has storage drawers 14 adapted to accommodate collecting bags for the liquid or other containers such as bags for sampling or drainage.

A pipe 8 is linked to a source bag (not shown) containing the liquid to treat and comprises a component adapted to cooperate with the pump 5 to make that liquid flow towards the filter components 9 and 11, passing via the pressure sensors 7 and 10. Another pipe 12 is connected to the filter component 11 to make that treated liquid flow towards the collecting bag positioned within a drawer 14.

Figure 2:
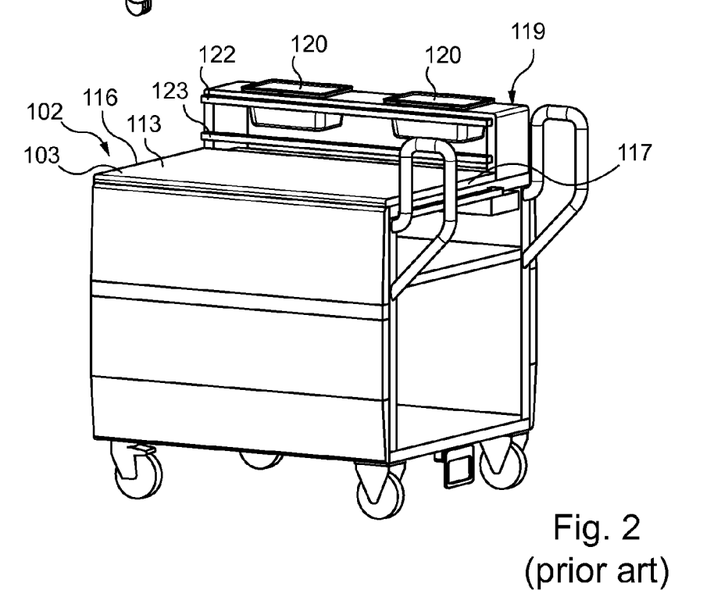

A second cart 102 illustrated in FIG. 2 is also known which is a variant embodiment of the second cart 2 of FIG. 1.

This second cart 102 is similar to the second cart 2 apart from the fact that it further comprises a metal structure 119 disposed rearwardly on the platform 103. This metal structure 119 is provided on the top with two containers 120 and on the front with two bars 122 and 123 which extend in the longitudinal direction of the second cart 102 between two opposite edges 116 and 117 of the second cart 102 that run front-to-back. The first bar 122 is an anchorage bar and the second bar 123 is a bearing bar for supports adapted to carry reusable and disposable components. Furthermore, platform 103 is formed by a plate of transparent material to make it possible to follow the progress of the filling of the collecting container with treated liquid.

The diversity of the treatments that may be performed on these installations is great, in particular depending on the selection by the user of the liquid to treat and on the degree of purity to obtain for the collected treated liquid.

This high diversity in the treatments requires the use of numerous re-usable and disposable components that are different from one treatment to the other (in particular the number of filter components may increase), and consequently the arrangement of those components is required to be simple and convenient.

The invention aims to provide an installation enabling the simple, convenient and economical implementation of treatments for biological liquid.

For this, the invention concerns an installation for treatment of biological liquid, comprising a pump, a filtration assembly, a pre-filtration assembly having an inlet point and an outlet point, a platform provided with an edge running front-to-back as well as a network for conveying liquid formed by a plurality of pipes configured to link said inlet point of said pre-filtration assembly to said pump and said outlet point of said pre-filtration assembly to said filtration assembly, characterized in that said pre-filtration assembly comprises a first pre-filtration component and a second pre-filtration component which are aligned in a front-to-back direction on said platform along said front-to-back edge and which are each provided with an inlet nozzle and an outlet nozzle, said inlet point belonging to a first T-shaped branching connector and said outlet point belonging to a second T-shaped branching connector, said installation comprises a first intermediate pipe connected to a branch of said first T-shaped connector and to said inlet nozzle of said first pre-filtration component, a second intermediate pipe connected to another branch of said first T-shaped connector and to said inlet nozzle of said second pre-filtration component, a third intermediate pipe connected to a branch of said T-shaped connector and to said outlet nozzle of said first pre-filtration component and a fourth intermediate pipe connected to another branch of said second T-shaped connector and to said outlet nozzle of said second pre-filtration component, said inlet nozzles and outlet nozzles and said first, second, third and fourth intermediate conduits being on an opposite side of said first and second pre-filtration components to said front-to-back edge of said platform.

The installation according to the invention has an arrangement which ensures, firstly, fast and simple mounting (and disassembly) of the installation by facilitating the connections of the flexible pipes and by limiting the crossing of those pipes.

The position of the first pre-filtration component and of the second pre-filtration component corresponds both to placing in line topographically and placing in parallel fluidically those first and second pre-filtration components relative to each other.

Topographically, this arrangement is particularly compact, which enables space to be liberated on the side of those first and second pre-filtration components. It is thus easy to obtain access thereto.

Consequently, it is possible to very simply and rapidly connect the first, second, third and fourth intermediate conduits to the respective inlet and outlet nozzles of the first and second pre-filtration components.

By virtue of the compactness of this arrangement, it is possible to bring other re-usable components, such as valves situated for example between the first and second pre-filtration components and the filtration assembly, nearer to those first and second pre-filtration components.

This arrangement thus also makes it possible to significantly reduce the length of the disposable conduits of the conveying network linking in particular such valves to the first and second pre-filtration components.

Thus, the volume of liquid inside the circuit of the installation is minimized.

The arrangement of the first, second, third and fourth intermediate conduits promotes the balancing of the inlet flow of liquid into the first and second pre-filtration components and of the outlet flow of liquid from those first and second pre-filtration components, for example by providing for the installation to be configured such that the sum of the lengths of the first intermediate pipe and of the third intermediate pipe is substantially equal to the sum of the lengths of the second intermediate pipe and of the fourth intermediate pipe.

This arrangement thus promotes the balancing of the pressure losses along the fluidic path going from the inlet point of the pre-filtration assembly to its outlet point passing via the first intermediate pipe, by the first pre-filtration component and by the third intermediate pipe and along the fluidic path going from the same inlet point to the same outlet point but passing via the second intermediate pipe, by the second pre-filtration component and by the fourth intermediate pipe.

Consequently, this arrangement, in fluidic terms, provides a very good distribution of the biological liquid within the pre-filtration assembly.

It therefore follows from the above that the installation for treatment of biological liquid according to the invention is particularly simple, convenient and economical.

According to preferred simple, convenient and economical features of the installation according to the invention:

said first pre-filtration component and said second pre-filtration component each have a lateral face from which project said respective inlet nozzle and said respective outlet nozzle;

said pre-filtration assembly is mounted on a first support placed on said platform;

said first support comprises a mounting from which projects a component provided with at least one member for receiving said first pre-filtration component and said second pre-filtration component and with at least one foot for bearing on said platform;

said platform comprises a metal structure disposed rearwardly and provided with an anchorage bar extending in a direction transverse to said front-to-back direction of said platform and said mounting of said first support has a channel-shaped upper part configured to come to rest on said anchorage bar;

said platform comprises a metal structure disposed rearwardly and provided with a bearing bar extending in a direction transverse to said front-to-back direction of said platform and said mounting of said first support has a lower part provided with at least one shoulder and configured to come to bear on said bearing bar;

said first support comprises a fastening plate mounted on said mounting and said component has a connection portion configured to be fastened onto said fastening plate;

said installation comprises a fifth intermediate pipe linked to said outlet point of said pre-filtration assembly and linked to said filtration assembly, a group of at least one valve situated on said fifth intermediate pipe and disposed on said platform facing said outlet point of said pre-filtration assembly and a pressure sensor situated on said fifth intermediate pipe between said group of at least one valve and said filtration assembly;

said group of at least one valve and said pressure sensor are mounted on the same second support placed on said platform in said front-to-back direction of said platform;

said second support comprises a mounting from which extends a component provided with at least one member for receiving said group of at least one valve and a member for receiving said pressure sensor and with at least one foot for bearing on said platform;

said platform comprises a metal structure disposed rearwardly and provided with an anchorage bar and a bearing bar extending in a direction transverse to said front-to-back direction of said platform and said mounting of said second support has a channel-shaped upper part configured to come to rest on said anchorage bar and a lower part provided with at least one shoulder and configured to come to bear against said bearing bar;

said installation comprises a filter cart provided with said platform;

said filtration assembly is disposed on said filter cart, the installation comprises a pump cart on which is disposed said pump and said filter cart is juxtaposed against said pump cart by said front-to-back edge of said platform;

said filter cart is configured to be nested at least partially in said pump cart; and/or said pump cart has a support platform for said pump configured such that said filter cart can be slid under and be positioned, at least partially, under said pump in nested configuration, in which nested configuration said pre-filtration assembly is positioned at least partially under said support platform of said pump cart.

The disclosure of the invention will now be continued with the description of embodiments, given below by way of illustrative and non-limiting example, with reference to the accompanying drawings, in which:

FIG. 1 is a diagram in perspective of an installation according to the state of the art, in separated configuration;

FIG. 2 is a diagram in perspective of a variant embodiment of the second cart of the installation of FIG. 1;

FIG. 3 is a diagrammatic view of the circuit of an installation for viral retention treatment according to the invention;

FIG. 4 is a diagram in perspective of the re-usable and disposable components of an installation in accordance with the invention adapted to be disposed on the first cart 1 of FIG. 1 and on the second cart 102 of FIG. 2; and

Figure 4:
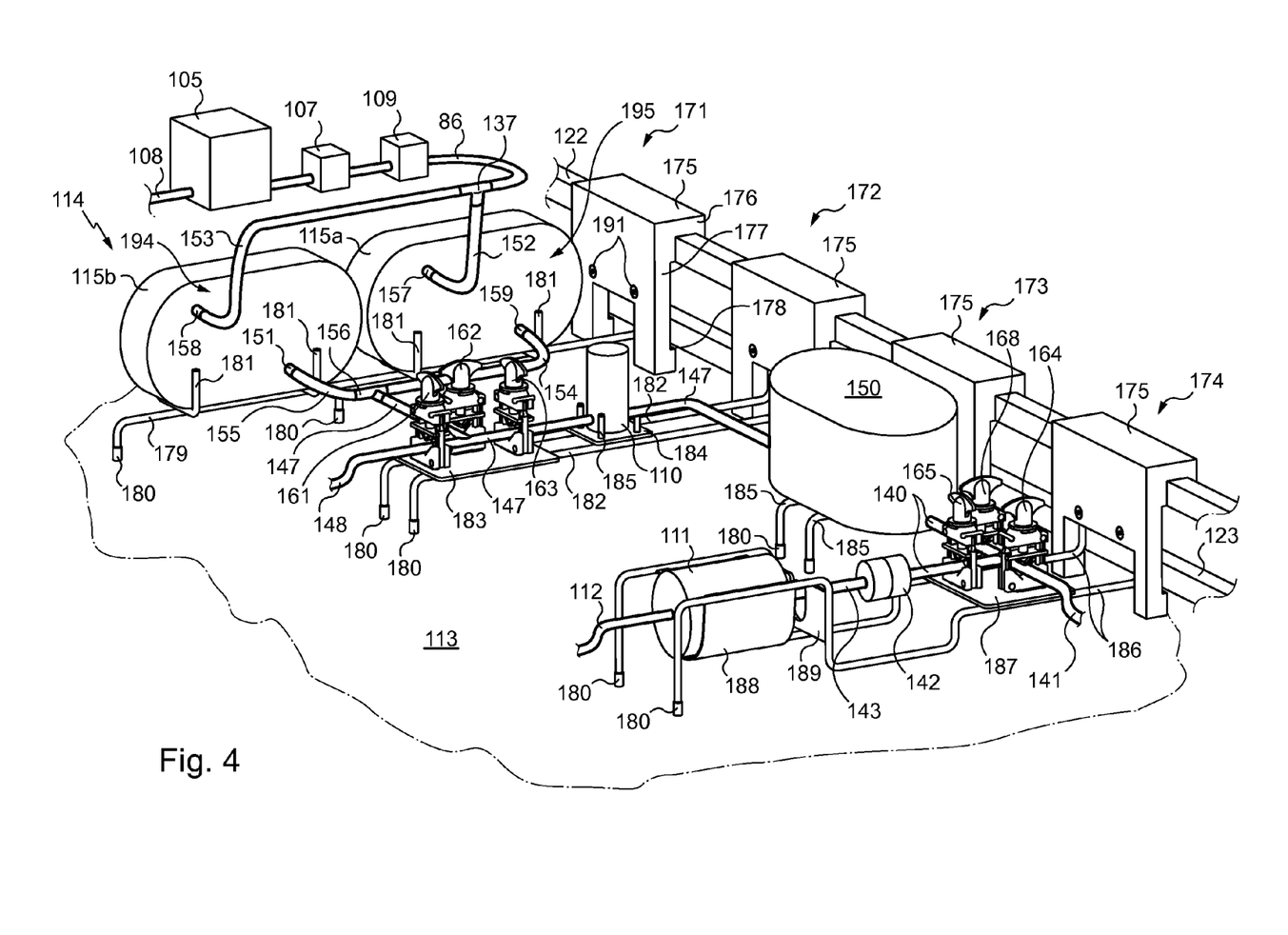

Referring to FIG. 4, there are shown re-usable and disposable components of an installation for treating a biological liquid by viral retention, which are adapted to be mounted on a first cart and a second cart that are not shown but which are similar respectively to the first cart 1 of FIG. 1 and to the second cart 102 of FIG. 2.

Figure 3:
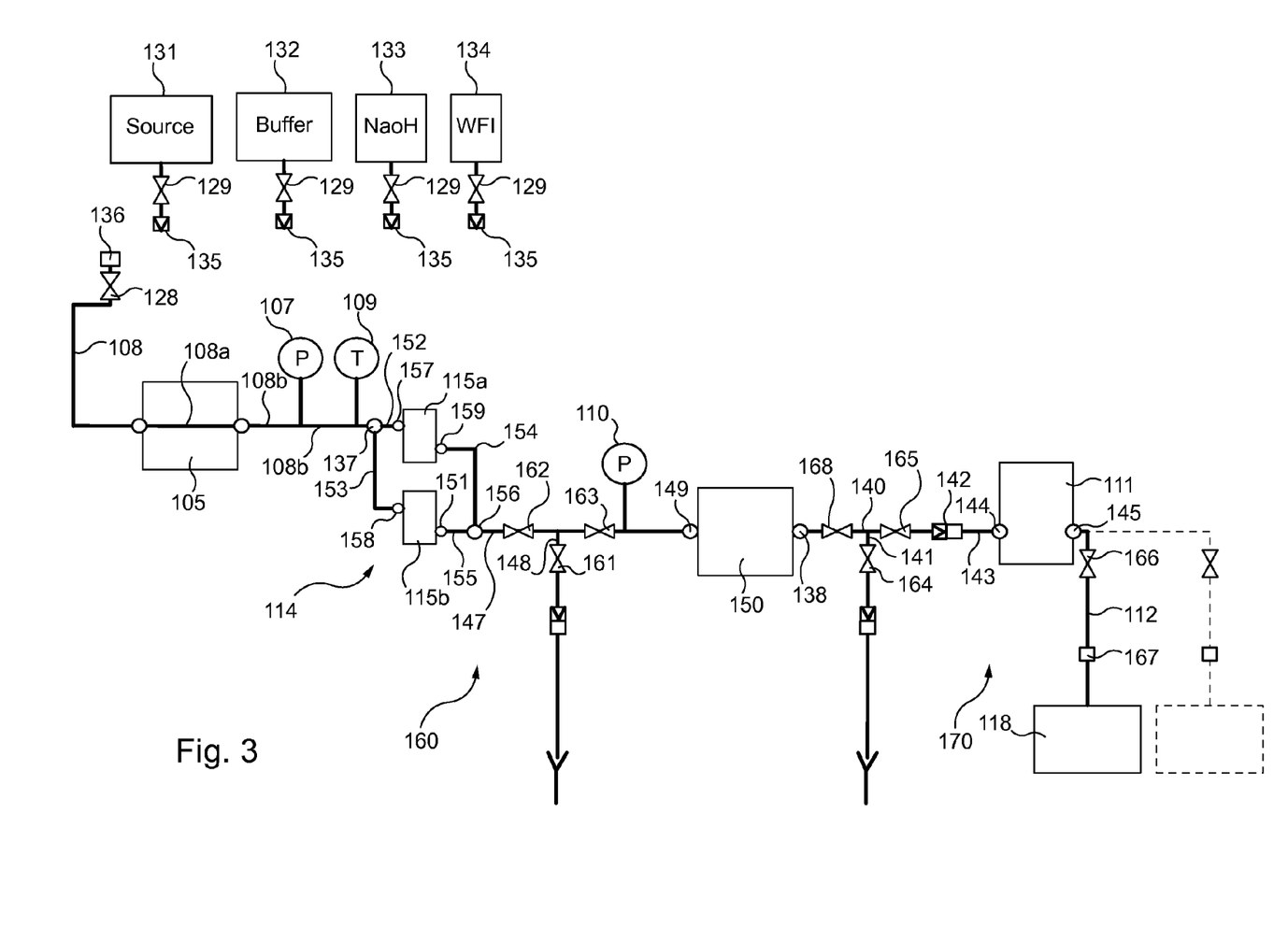

With reference to FIG. 3, a description will first of all be made of the circuit for treating a biological liquid, produced using re-usable and disposable components installed on the first cart 1 and on the second cart 102, in the case of a treatment by viral retention.

The product to be treated is initially in a source bag 131, filled with liquid from the culture bioreactor or from the previous treatment.

This source bag 131 is connected via a male connector 135 to a first circuit section 160 which extends from the source bag 131 to an inlet point 149 of a virus filtration component 150.

The male connector 135 is connected to a first main disposable flexible pipe 108, which is itself provided with a female connector 136.

To the first flexible pipe 108 the operator can connect other bags 132,133 or 134 containing products such as a buffer liquid, sodium hydroxide (NaOH) or a rinsing liquid such as pure water, respectively, for managing the cleanliness of the circuit or for pushing the liquid through the components that provide the treatment.

These bags 132 to 134 are also provided with a male connector 135 adapted to cooperate with the female connector 136 of the first flexible pipe 108.

Isolating valves 128 and 129 are furthermore fitted onto the flexible pipes upstream and downstream of the connectors 135, 136 to enable or prevent flow of the liquid in the first pipe 108.

When the valves 129 and 128 are open and a pump 105 is operating, which is a peristaltic pump here, the biological liquid is sucked from the source bag 131 and passes into the first pipe 108.

This first pipe 108 has a portion 108a adapted to cooperate with the flow pump 105.

The first pipe 108 has a portion 108b, downstream of the flow pump 105, which is linked to a first pressure sensor 107 and to a temperature sensor 109, which sensors 107 and 109 respectively measure the value of the pressure and the value of the temperature upstream of a pre-filtration assembly 114.

At its other end, the portion 108b of the first pipe 108 is linked to an inlet point of the pre-filtration assembly 114, which inlet point belongs to a first T-shaped branching connector 137.

This pre-filtration assembly 114 comprises two identical pre-filtration components 115a and 115b which are mounted in parallel to commence the virus retention operation.

The inlet point is situated at a first branch of the first T-shaped branching connector 137 which is connected to the end of the portion 108b of the first pipe 108, and of which a second branch is connected to a first intermediate pipe 152 and a third branch is connected to a second intermediate pipe 153.

The first intermediate pipe 152 is connected to an inlet nozzle 157 of the first pre-filtration component 115a and communicates with an inlet aperture of that inlet nozzle 157.

The second intermediate pipe 153 is connected to an inlet nozzle 158 of the second pre-filtration component 115b and communicates with an inlet aperture of that inlet nozzle 158.

The liquid to treat, still under the action of the flow pump 105, passes through each pre-filtration component 115a, 115b and respectively exits therefrom by an outlet aperture provided in an outlet nozzle 159 of the first pre-filtration component 115a and by an outlet aperture provided in an outlet nozzle 151 of the second pre-filtration component 115b.

The liquid next flows to an outlet point of the pre-filtration assembly 114.

This outlet point belongs to a second T-shaped branching connector 156 a first branch of which is connected to a third intermediate pipe 154, a second branch is connected to a fourth intermediate pipe 155 and a third branch is connected to a fifth intermediate pipe 147.

The third intermediate pipe 154 is connected to the outlet nozzle 159 of the first pre-filtration component 115a.

The fourth intermediate pipe 155 is connected to the outlet nozzle 151 of the second pre-filtration component 115b.

The fifth intermediate pipe 147 has a third T-shaped branching connector from which leads a sixth intermediate pipe 148 provided with an isolating valve 161.

This sixth intermediate pipe 148 has a male connector at its end capable of being connected to an adapted female connector, which is carried by a pipe for evacuation to the drain, or even by a sampling bag or drainage bag.

The fifth intermediate pipe 147 furthermore has an isolating valve 162 disposed between its T-shaped branching connector and the outlet point of the pre-filtration assembly 114.

The fifth intermediate pipe 147 is furthermore connected at its end to an inlet point 149 of a viral filtration component 150 which is adapted to terminate the virus retention operation.

This fifth intermediate pipe 147 is provided with an isolating valve 163 between its T-shaped branching connector and the inlet point 149.

This fifth intermediate pipe 147 is then linked to a second pressure sensor 110.

The viral filtration component 150 has an outlet point 138 to which a second circuit section 170 is connected which extends from the outlet point 138 to a collecting bag 118.

On leaving this viral filtration component 150, the liquid flows into a seventh intermediate pipe 140 connected to the outlet point 138 and provided with an isolating valve 168.

The seventh intermediate pipe 140 has a fourth T-shaped branching connector from which leads an eighth intermediate pipe 141 provided with an isolating valve 164.

This eighth pipe 141 has a male connector at its end capable of being connected to a suitable female connector, which is carried by a pipe for evacuation to the drain, or even by a sampling bag or drainage bag.

The operator uses these bags if he needs to take a sample of the liquid for analysis or to drain the liquid contained in the circuit.

The seventh intermediate pipe 140 ends with a male connector 142 to which is connected a female connector fastened to one end of a ninth intermediate pipe 143.

This seventh intermediate pipe 140 is provided with an isolating valve 165 between its T-shaped branching connector and the male connector 142.

The ninth intermediate pipe 143 is linked at its other end to an inlet point 144 for a final filtration component 111.

The liquid to treat passes through this final filtration component 111 to ensure the sterility of the treated liquid.

The final filtration component 111 and the viral filtration component 150 form a filtration assembly.

On leaving this final filtration component 111, the biological liquid passes into a second flexible main pipe 112, which is linked to an outlet point 145 of that final filtration component 111.

This second pipe 112 is provided with an isolating valve 166 for enabling or preventing flow of the liquid.

Its other end is connected directly to the collecting bag 118 which is intended for collecting the treated liquid.

Near the bag 118, the second pipe 112 includes a Millipore NovaSeal™ type component, adapted to be crimped and cut in one operation.

T-shaped branching connectors can also be provided on this second pipe 112 for connecting sampling bags or draining bags or tanks (in dashed line) to it, as required. An isolating valve and the same component of NovaSeal™ type may also be provided thereon.

The installation that uses the circuit described above is described next with reference to FIGS. 4 to 6. The first cart and the second cart are not shown but as indicated above, the re-usable and disposable components of FIG. 4 are adapted to be disposed on a first cart similar to the first cart 1 of FIG. 1 and on a second cart similar to the second cart 102 of FIG. 2.

The pump 105, the first pressure sensor 107 and the temperature sensor 109 are mounted on the platform 4 of the first cart 1.

The first pipe 108 coming from the source bag is connected to the pump 105, of which first pipe 108 the portion 108b passes through the first pressure sensor 107 and the temperature sensor 109 and leads towards the pre-filtration assembly 114 on the second cart 102.

The pre-filtration assembly 114 is disposed in a front-to-back direction on the upper face 113 of the platform 103 of the second cart 102, along the front-to-back edge 116 of that platform 103.

This pre-filtration assembly 114 is mounted on a first support 171 which is anchored to the anchorage bar 122 of the second cart 102 and which rests on the upper face 113.

This first support 171 for the pre-filtration assembly 114 has a mounting 175 of plastics material having a channel-shaped upper part 176 the inside of the channel of which is configured to rest on the anchorage bar 122 and a lower part 177 which is provided with two pillars each having a shoulder 178 at the bottom of that lower part 177.

A space is defined between the two pillars of this lower part 177.

The pillars of the lower part 177 are adapted to come to bear against the bearing bar 123 of the second cart 102, each shoulder 178 being adapted to come against a lower edge of that bearing bar 123 in order to hold the mounting 175 on the metal structure 119 of the second cart 102.

The mounting 175 is suspended such that it does not rest on the upper face 113.

The first support 171 furthermore has a metal rod 179 which projects from the mounting 175.

Figure 5:
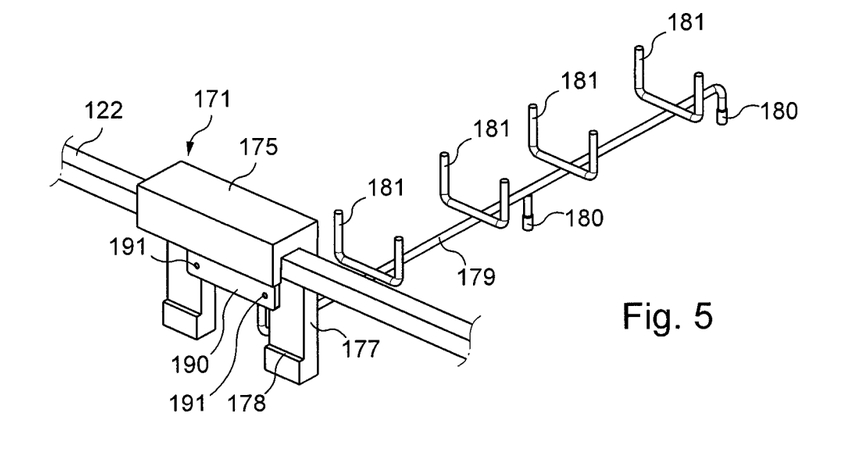
FIGS. 5 and 6 are diagrams in perspective of the re-usable supports comprised by the components illustrated in FIG. 4.
Figure 6:
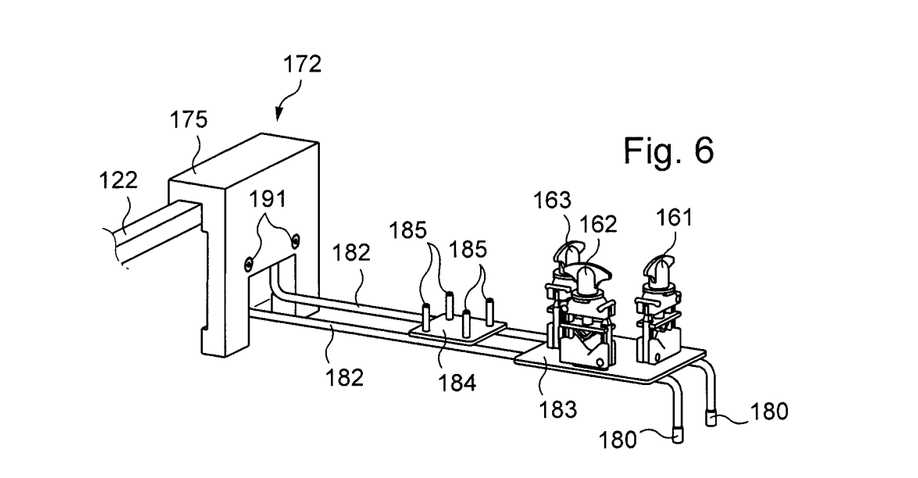

The metal rod 179 has an attaching portion (not visible) configured to be welded onto a fastening plate 190 screw mounted onto the back of the mounting 175 (FIG. 5).

The mounting 175 and the plate 190 are fastened together by screws 191.

The rod 179 extends from the mounting 175, from one side of the space passing along one pillar, towards the front of the platform 103 and has two vertical bearing feet 180 which rest on the upper face 113.

This rod 179 furthermore has four U-shaped metal parts 181 regularly spaced from each other along the rod 179.

The separation between the branches of the U of each part 181 and the distance separating two successive parts 181 are determined such that pairs of those parts 181 are able to receive a respective pre-filtration component 115a, 115b.

Thus, the first and second pre-filtration components 115a, 115b are each received on the metal rod 179 in two parts 181, forming receiving members.

These pre-filtration components 115a and 115b are thus aligned in a front-to-back direction along the front-to-back edge 116 of the platform 103.

These first and second pre-filtration components 115a and 115b each have a respective inlet nozzle 157, 158 and a respective outlet nozzle 159, 151 which are disposed on an opposite side of the first and second pre-filtration components 115a, 115b to the front-to-back edge 116 of the platform 103.

The inlet nozzles 157, 158 and outlet nozzles 159, 151 are here disposed in diagonal relationship on the respective face 195, 194 of the first and second pre-filtration components 115a, 115b.

The first T-shaped branching connector 137 which comprises the inlet point of the pre-filtration assembly 114 is disposed in the vicinity of the inlet nozzle 157 of the first pre-filtration component 115a.

The second T-shaped branching connector 138 which comprises the outlet point of the pre-filtration assembly 114 is situated in the vicinity of the outlet nozzle 151 of the second pre-filtration component 115b.

The portion 108b of the first main pipe 108 extends to the inlet point of the first T-shaped branching connector 137.

The first intermediate pipe 152 extends from a branch of that connector 137 to the inlet nozzle 157 of the first pre-filtration component 115a and the second intermediate pipe 153 extends from another branch of the connector 137 to the inlet nozzle 158 of the second pre-filtration component 115b.

The third intermediate pipe 154 extends from the outlet nozzle 159 of the first pre-filtration component to a branch of the second T-shaped branching connector 156 and the fourth intermediate pipe 155 extends from the outlet nozzle 151 of the second pre-filtration component 115b to another branch of that connector 156.

The third branch of this connector 156 corresponds to the outlet point of the pre-filtration assembly 114 to which the fifth intermediate pipe 147 connects and leads towards the isolation valve 162, which is situated facing the second branching connector 156, and in particular the outlet point of the pre-filtration assembly 114.

The valve 162 forms part of a group of valves comprising two other valves 161 and 163 mounted on a second support 172 disposed beside the first support 171 facing the respective faces 194 and 195 of the first and second pre-filtration components 115a and 115b.

It can be clearly seen that it is particularly convenient to connect the intermediate conduits 152 to 155 to the pre-filtration components 115a and 115b on account of the space which is freed on the side of those components.

On the second support 172 the second pressure sensor 110 is also mounted.

The second pressure sensor 110 is a sensor of the type as described in document EP 2 228 635.

The group of valves 161 to 163 and the sensor 110 are aligned in the front-to-back direction on the upper face 113.

The second support 172 has a mounting 175 in every way identical to the mounting 175 of the first support 171.

This second support 172 is thus anchored to the anchorage bar 122 and bears against the bearing bar 123.

The second support 172 differs from the first support 171 in that it comprises two metal rods 182 which each project from the mounting 175 at the location of the two lower parts 177, that is to say on respective opposite sides of the space formed between those two parts 177.

The two rods 182 extend in parallel towards the front of the upper face 113 and each has a bearing foot 180 which rests on that upper surface 113.

At the end of these rods 182, towards the front, a support plate 183 is rigidly attached on which the valves 161 to 163 are mounted.

This support plate 183 forms a reception member.

Between that plate 183 and the mounting 175, another plate 184 is fastened to the rods 182.

This plate 184 has four vertically extending studs 185 which define a reception space for the second pressure sensor 110.

This plate 184 forms a reception member.

The fifth intermediate pipe 147 passes via the third T-shaped connector at the location of the valve 162 and the valve 163, extends to the second pressure sensor 110 and continues to the viral filtration component 150.

The sixth pipe 148, which passes through the valve 161, leaves from the third T-shaped branching connector on the fifth intermediate pipe 147.

The viral filtration component 150 is mounted on a third support 173 disposed beside the second support 172 towards the front-to-back edge 117 of the platform 103.

This third support 173 has a mounting 175 identical to the mounting 175 of each of the supports 171 and 172.

This third support 173 is thus anchored to the anchorage bar 122 and bears against the bearing bar 123.

The third support 173 differs from the second support 172 in that it has two rods 185 shorter than the two rods 182 of the second support structure 172.

These two metal rods 185 are provided at their ends with two bearing feet 180 placed on the upper surface 113.

This third support 173 furthermore has a support plate (not visible) for the viral filtration component 150, on which plate the viral filtration component 150 is placed.

The fifth pipe 147 enters the viral filtration component 150 by its inlet point and it is the seventh intermediate pipe 140 which extends from the outlet point of that viral filtration component 150 to the valve 168.

This valve 168 forms part of another group of valves further comprising the valves 164 and 165.

These valves 164, 165 and 168 are mounted on a fourth support 174, the valve 168 facing the viral filtration component 150.

This fourth support 174 has a mounting 175 identical to the mountings 175 of the supports 171, 172 and 173.

This fourth support 174 is thus anchored to the anchorage bar 122 and bears against the bearing bar 123.

The fourth support 174 is disposed beside the third support 173, in the vicinity of the front-to-back edge 117 of the platform 103.

This fourth support 174 is of substantially equal length to the length of the second support 172.

This fourth support 174 differs from the second support 172 in that it comprises two metal rods 186 having a first portion extending in a first horizontal plane, a second portion extending in a second horizontal plane situated lower than the first horizontal plane and a third portion extending in a third horizontal plane situated higher than the first horizontal plane and the second horizontal plane.

These two metal rods 186 are each provided at their end with a bearing foot 180 which rests on the upper face 113.

At the location of the first portion of the rods 186 a support plate 187 is fastened, forming a reception member, which is adapted to support the group of valves 164, 165 and 168.

At the location of the third portion of the rods 186 is disposed a support 188 in the form of a hammock, forming a reception member, attached to each rod 186, into which support 188 the final filtration component 111 is introduced.

A screen-forming plate 189 is furthermore fastened to the support 174 at the location of a vertical portion of the rods 186 joining the second portion and the third portion of those rods 186.

This screen-forming plate 189 has a cut-out for the passage of the ninth intermediate pipe 143.

The male connector 142 situated at the end of the seventh pipe 140 is to be found at the location of the second portion of the rods 186.

Thus, at the location of the valve 168 and of the valve 165, this seventh pipe 140 passes via the fourth T-shaped branching connector to the male connector 142.

The eighth pipe 141 leaves from the fourth T-shaped branching connector at the location of the seventh pipe 140 and passes by valve 164.

To the male connector 142 is connected the female connector fastened at the end of the ninth intermediate pipe 143 which passes through the cut-out of the plate 189 to reach the final filtration component 111.

The second flexible main pipe 102 extends from an outlet point of that filtration component 111.

The liquid to treat flows in the first main pipe 108 downstream of the flow pump 105, from the first pressure sensor 107 and from the temperature sensor 109, towards the pre-filtration assembly 114, and is then subjected to pressure measurement by the first pressure sensor 107 and temperature measurement by the temperature sensor 109.

At the location of the first branching connector 137, the liquid is divided into the first intermediate pipe 152 and into the second intermediate pipe 153.

The liquid next passes through the two pre-filtration components 115a and 115b and respectively comes out therefrom to enter respectively the third intermediate pipe 153 and the fourth intermediate pipe 154 until the second branching connector 156 is reached where the liquids meet then flow into the fifth intermediate pipe 147.

Thanks to the arrangement of the branching connectors 137 and 156 and of the inlet and outlet nozzles of the pre-filtration components 115a and 115b, a good distribution of the liquid is ensured entering and coming out from the pre-filtration assembly 114.

The liquid next flows in the fifth intermediate pipe 147 via the group of valves 161, 162 and 163 where it is subjected to pressure measurement by the second pressure sensor 110 just before entering the viral filtration component 150.

Since the second pressure sensor 110 is in the vicinity of the viral filtration component 150, the measurement is particularly precise.

The liquid next passes through the viral filtration component 150 and comes out from it into a seventh intermediate pipe 140 leading to the male connector 142 via the group of valves 164, 165 and 168, which connector 142 is connected to a female connector in order for the liquid then to pass into the ninth intermediate pipe 143 leading to the final filtration component 111.

The liquid next passes through that final filtration component 111 and comes out from it into the second flexible main pipe 112.

The liquid is next sent into the collecting bag positioned in the cart 102.

In variants that are not illustrated:

the pre-filtration assembly does not have two pre-filtration components formed by two separate parts, but rather by two pre-filtration components integrated into the same casing;

the supports for the re-usable and disposable components do not have a mounting of plastics material and one or more rods and receiving members of metal material, but those supports are instead completely of plastics material or completely of metal material;

the supports for the re-usable and disposable components do not have any rod, by rather an unperforated plate;

the mountings of the supports for re-usable and disposable components are not suspended, but those mountings have instead a lower part which is placed on the upper face of the platform.

the supports for the re-usable and disposable components do not have a mounting and a component which projects from that mounting but are instead formed by a block which over a major part of its length rests on the upper face of the platform;

the members for reception of the first and second pre-filtration components are not formed by U-shaped rods, but rather by a container or a plate; and the pressure sensor support does not have any stud but that support is instead formed by a hollow cylinder or a flat plate without any stud.

It should be noted more generally that the invention is not limited to the examples described and represented.

The invention claimed is:

1. An installation for treatment of biological liquid, comprising a pump, a filtration assembly, a pre filtration assembly having an inlet point and an outlet point, a platform provided with an edge running front-to-back as well as a network for conveying liquid formed by a plurality of pipes configured to link said inlet point of said pre-filtration assembly to said pump and said outlet point of said pre-filtration assembly to said filtration assembly, wherein said pre-filtration assembly comprises a first pre-filtration component and a second pre-filtration component which are aligned in a front-to-back direction on said platform along said front-to-back edge and which are each provided with an inlet nozzle and an outlet nozzle, said inlet point belonging to a first T-shaped branching connector and said outlet point belonging to a second T-shaped branching connector, said installation comprises a first intermediate pipe connected to a branch of said first T-shaped connector and to said inlet nozzle of said first pre-filtration component, a second intermediate pipe connected to another branch of said first T-shaped connector and to said inlet nozzle of said second pre-filtration component, a third intermediate pipe connected to a branch of said T-shaped connector and to said outlet nozzle of said first pre-filtration component and a fourth intermediate pipe connected to another branch of said second T-shaped connector and to said outlet nozzle of said second pre-filtration component, said inlet nozzles and outlet nozzles and said first, second, third and fourth intermediate pipes being on an opposite side of said first and second pre-filtration to said front-to-back edge of said platform.

2. An installation according to claim 1, wherein said first pre-filtration component and said second pre-filtration component each have a lateral face from which project said respective inlet nozzle and said respective outlet nozzle.

3. An installation according to claim 1, wherein said pre-filtration assembly is mounted on a first support placed on said platform.

4. An installation according to claim 3, wherein said first support comprises a mounting from which projects a component provided with at least one member for receiving said first pre-filtration component and said second pre-filtration component and with at least one foot for bearing on said platform.

5. An installation according to claim 4, wherein said platform comprises a metal structure disposed rearwardly and provided with an anchorage bar extending in a direction transverse to said front-to-back direction of said platform and said mounting of said first support has a channel-shaped upper part configured to come to rest on said anchorage bar.

6. An installation according to claim 4, wherein said platform comprises a metal structure disposed rearwardly and provided with a bearing bar extending in a direction transverse to said front-to-back direction of said platform and said mounting of said first support has a lower part provided with at least one shoulder and configured to come to bear on said bearing bar.

7. An installation according to claim 4, wherein said first support comprises a fastening plate mounted on said mounting and said component has a connection portion configured to be fastened to said fastening plate.

8. An installation according to claim 1, further comprising a fifth intermediate pipe linked to said outlet point of said pre-filtration assembly and linked to said filtration assembly, a group of at least one valve situated on said fifth intermediate pipe and disposed on said platform facing said outlet point of said pre-filtration assembly and a pressure sensor situated on said fifth intermediate pipe between said group of at least one valve and said filtration assembly.

9. An installation according to claim 8, wherein said group of at least one valve and said pressure sensor are mounted on the same second support placed on said platform in said front-to-back direction of said platform.

10. An installation according to claim 9, wherein said second support comprises a mounting from which extends a component provided with at least one member for receiving said group of at least one valve and a member for receiving said pressure sensor and with at least one foot for bearing on said platform.

11. An installation according to claim 9, wherein said platform comprises a metal structure disposed rearwardly and provided with an anchorage bar and a bearing bar extending in a direction transverse to said front-to-back direction of said platform and said mounting of said second support has a channel-shaped upper part configured to come to rest on said anchorage bar and a lower part provided with at least one shoulder and configured to come to bear against said bearing bar.

12. An installation according to claim 1, further comprising a filter cart provided with said platform.

13. An installation according to claim 12, wherein said filtration assembly is disposed on said filter cart, the installation comprises a pump cart on which is disposed said pump and said filter cart is juxtaposed against said pump cart by said front to back edge of said platform.

14. An installation according to claim 13, wherein said filter cart is configured to be nested at least partially in said pump cart.

15. An installation according to claim 14, wherein said pump cart has a support platform for said pump configured such that said filter cart can be slid under and be positioned, at least partially, under said pump in nested configuration, in which nested configuration said pre-filtration assembly is positioned at least partially under said support platform of said pump cart.

* * * * *

UNITED STATES PATENT AND TRADEMARK OFFICE
CERTIFICATE OF CORRECTION

| | |
|---|---|
| PATENT NO. | : 8,916,045 B2 |
| APPLICATION NO. | : 13/430734 |
| DATED | : December 23, 2014 |
| INVENTOR(S) | : Reinbigler et al. |

Page 1 of 1

It is certified that error appears in the above-identified patent and that said Letters Patent is hereby corrected as shown below:

In the claim

Column 11, line 56, claim 1 delete "pre-filtration to" and insert -- pre-filtration components to -- therefor.

Signed and Sealed this
Twenty-first Day of April, 2015

Michelle K. Lee
*Director of the United States Patent and Trademark Office*